United States Patent
Apert et al.

(10) Patent No.: US 6,794,555 B2
(45) Date of Patent: Sep. 21, 2004

(54) ANTISEPTIC COMPRESS

(75) Inventors: Laurent Apert, Dijon (FR); Stéphane Auguste, Varois et Chaignot (FR)

(73) Assignee: Laboratoires d'Hygiene et de Dietetique, Chenove (FR)

( * ) Notice: Subject to any disclaimer, the term of this patent is extended or adjusted under 35 U.S.C. 154(b) by 120 days.

(21) Appl. No.: 10/239,125

(22) PCT Filed: Mar. 21, 2001

(86) PCT No.: PCT/FR01/00834

§ 371 (c)(1),
(2), (4) Date: Sep. 18, 2002

(87) PCT Pub. No.: WO01/70285

PCT Pub. Date: Sep. 27, 2001

(65) Prior Publication Data

US 2003/0036717 A1 Feb. 20, 2003

(30) Foreign Application Priority Data

Mar. 22, 2000 (FR) .............................. 00 03665

(51) Int. Cl.$^7$ ..................... A61F 13/00; A61F 15/16; A61K 13/74

(52) U.S. Cl. ............................. 602/48; 602/42; 602/43; 424/445; 424/447; 424/448; 424/78.06

(58) Field of Search ............. 602/41–59; 604/304–308; 424/443–449, 400, 78.06

(56) References Cited

U.S. PATENT DOCUMENTS

| 6,039,940 A | | 3/2000 | Perrault et al. | |
| 6,375,977 B1 | * | 4/2002 | Auguste et al. | ............. 424/447 |
| 2002/0147265 A1 | * | 10/2002 | Ding et al. | ................. 524/501 |
| 2003/0175333 A1 | * | 9/2003 | Shefer et al. | ............... 424/449 |

FOREIGN PATENT DOCUMENTS

| FR | 2 753 380 | 3/1998 |
| FR | 2 775 903 | 9/1999 |
| GB | 1 599 159 | 9/1981 |
| GB | 2 098 074 | 11/1982 |
| WO | WO 95/17166 | 6/1995 |

* cited by examiner

*Primary Examiner*—Kim M. Lewis
(74) *Attorney, Agent, or Firm*—Merchant & Gould P.C.

(57) ABSTRACT

The compress is of the type including a contact surface with the wound or burn which has an elastomeric matrix highly plasticized with a non-polar oil or grease, the elastomeric matrix containing a hydrocolloid in dispersion. The elastomeric matrix also contains, in dispersion, at least one antiseptic and at least one surfactant with a hydrophilic/lipophilic balance (HLB) greater than 10. The invention is applicable particularly to compresses and dressings.

9 Claims, No Drawings

ANTISEPTIC COMPRESS

The present invention relates to an antiseptic compress for promoting the healing of infected wounds or wounds susceptible to infection, and to a dressing incorporating the antiseptic compress.

PRIOR ART

It is already known that dressings capable of maintaining a certain moisture level on the surface of a wound have a favorable action on the healing process. This property is utilized in numerous dressings, for example "ALGOPLAQUE" marketed by Laboratoires URGO or "COMFEEL" marketed by COLOPLAST, which use a dispersion of hydrocolloids in an adhesive hydrophobic matrix; in these dressings the hydrocolloid particles absorb the exudates and maintain a moist environment favorable to healing. However, in the case of highly exudative wounds, the absorption is inadequate and it is possible to observe an accumulation of fluids which are likely rapidly to become a focus of infection.

Another type of dressing, known as a tulle gras, uses greases and oils, such as officinal petrolatum and paraffin, to form a wound protection. Absorption of the exudates is not possible here and a compress has to be provided in the case of weeping wounds. In other cases the wound tends to dry and adhesions are then frequently observed between the dressing and the freshly regenerated tissues. This entails painful renewal of the dressing, if not destruction of the scar tissues. To avoid the problems of infection in wounds, it is known to add antiseptics to the dressing in order to limit or, preferably, reduce the development of infectious pathogens. Dressings are known in this field which contain antiseptics dispersed in an ointment based on hydrophobic fats, an example of such a dressing being UNITUL marketed by BAMA-GEVE. Also, EP-A-689425 discloses a hydrating gel comprising a hydrocolloid system based on alginate and sodium carboxymethyl cellulose and a preservative system consisting of antimicrobials and antifungals. Said gel is a hydrogel containing a high proportion of water (97%), in which the active agents are in solution. A similarly formulated dressing with the mark CONNETIVINA PLUS, marketed by FIDIA, is also known; this consists of a hydrogel based on polyethylene glycol and contains silver sulfadiazine in dispersion and a hyaluronic acid salt.

FR 2 775 903 is also known and describes an adhesive hydrocolloid mass for dressings, the absorption capacity of which is amplified and accelerated by the combined presence of a hydrocolloid and a surfactant. This adhesive mass can additionally contain an antiseptic, which can easily be diffused when the dressing has absorbed an aqueous fluid capable of partially dissolving said antiseptic.

In the case of dressings which have a hydrophobic contact layer based especially on fats or elastomers, it is much more difficult to obtain an antiseptic action by means of active substances dispersed in the contact layer. These active substances are trapped in the hydrophobic structure and therefore possess an extremely low bioavailability. This problem is exacerbated when using poorly absorbent or non-absorbent dressing structures comprising fairly cohesive elastomers in order to prevent the dressing structure from breaking down when the dressing is removed from the wound. For this reason there are no dressings at the present time which contain both synthetic elastomers and antiseptics in a non-adhesive and non-absorbent contact layer.

SUBJECT OF THE INVENTION

The aim of the present invention is to provide a non-adhesive and poorly absorbent contact compress for skin wounds or burns susceptible to infection, said compress being based on fats and hydrocolloids, and a dressing incorporating such a compress.

DESCRIPTION

It has been found according to the invention that it is possible to obtain a compress consisting of a non-adhesive, amphiphilic, cohesive contact layer and having an antiseptic action. It has in fact been found that the bioavailability of the antiseptics dispersed in the contact layer can be considerably improved in the presence of a non-ionic surfactant with a hydrophilic/lipophilic balance (HLB) greater than 10.

The compress according to the invention, consisting of a cohesive structure based on synthetic elastomers of the tri-block type highly plasticized with a non-polar oil, is characterized in that it contains, in dispersion, a small amount of hydrocolloids, at least one antiseptic and at least one surfactant with a hydrophilic/lipophilic balance (HLB) greater than 10.

According to one particular feature of the invention, the synthetic elastomers are tri-block elastomers with a saturated central block, such as a copolymer of polystyrene blocks and polyethylene-butylene blocks (SEBS) or a copolymer of polystyrene blocks and polyethylene-propylene blocks (SEPS).

According to another particular feature of the invention, the non-polar oil is a paraffin oil, an officinal petrolatum or a mixture of these compounds.

According to another particular feature of the invention, the hydrocolloids are present in the form of sodium carboxymethyl cellulose (CMC).

According to another particular feature of the invention, the surfactant is of the non-ionic type and is selected from polyethoxylated derivatives of sorbitol fatty acid esters.

According to another particular feature of the invention, the antiseptics are antimicrobial active substances and/or antifungal active substances preferably selected from silver salts.

In a preferred embodiment of the invention, the wound-contacting layer is discontinuous and preferably consists of an open-mesh woven fabric totally coated with a non-adhesive cohesive gel so as to leave the meshes essentially unobstructed, said gel being formed of a highly plasticized, hydrophobic elastomeric matrix containing a dispersion of hydrocolloids, at least one antiseptic and at least one surfactant with a hydrophilic/lipophilic balance (HLB) greater than 10.

DETAILED DESCRIPTION

The antiseptic compress according to the invention comprises a wound-contacting layer essentially consisting of a non-adhesive cohesive Gel in which hydrocolloids, one or more antiseptics and a surfactant with a hydrophilic/lipophilic balance (HLB) greater than 10 are dispersed.

The cohesive gel, which serves to constitute the structure of the contact layer and assure the non-adhesive character of the dressing, consists of an elastomeric matrix, preferably based on tri-block elements, associated with a large amount of a non-polar oil or fat which will act simultaneously as plasticizer for the elastomeric material and as antiadhesive. This produces a non-adhesive cohesive gel which is very elastic, very easily shaped and very resistant to tearing.

It is preferable to use elastomers of the high molecular weight SEBS or SEPS type, for example those marketed by SHELL under the reference Kraton G 1651 or by KURARAY under the name SEPTON. These elastomers are present in the contact layer in an amount of about 3 to 8% by weight.

By specifically choosing these tri-block elastomers, it is possible to obtain a gel which is devoid of adhesiveness and perfectly antiadhesive towards the regenerated tissues and perilesional skin.

The non-polar oil is generally a mineral oil or mixture of mineral oils based on hydrocarbons, which can be fluid or more or less thick.

Within the framework of the invention, it will be preferable to use a paraffin oil, an officinal petrolatum or a mixture of these compounds.

It will be particularly preferable to use one or more mineral oils marketed by SHELL under the name ONDINA, preferably under the reference ONDINA 15, either alone or, advantageously, in a mixture with an officinal petrolatum as defined in the French pharmacopeia.

The non-polar oil is present in an amount of about 55 to 90% of the weight of the contact layer.

The compress also comprises a small amount of hydrocolloids in dispersion in the elastomeric matrix, a preferred hydrocolloid being sodium carboxymethyl cellulose (CMC), the function of which is to maintain a moist environment favorable for the healing process. In the case where sodium CMC is used, it is present in the form of a fine powder with a particle size of about 50 to 100 $\mu$m, in an amount of about 3 to 20%, preferably of about 4 to 14%, of the weight of the contact layer. Although small, this amount of hydrocolloid is sufficient to maintain a moisture level on the surface in contact with the wound without making the compress very absorbent, and makes it possible to prevent the contact layer from swelling.

In particular, the compresses according to the invention have a negligible or very low absorption capacity towards aqueous fluids and the increase in weight when they are brought into contact with water is minimal, being generally less than 50% and preferably less than 25% of the weight of the contact layer.

Within the framework of the invention, other hydrocolloids, for example alginates, can be used instead of CMC.

The contact layer also contains antiseptics in dispersion in the elastomeric material. The chosen active substances are those known for their antimicrobial or antifungal properties, especially compounds which are active in combating the development of pathogenic germs, for example *Staphylococcus aureus* (golden staphylococcus) or *Pseudomonas aeruginosa* (pyocyanic organism).

Among these active substances, which can be used alone or in combination, preference is given to chlorhexidine, hexamidine, betadine or silver salts such as silver sulfadiazine, silver chloride or silver nitrate. The amount present in the contact layer depends on the nature of the active principle and varies between 0.2 and 5%.

According to the invention, at least one surfactant is added in order to ensure that the resulting activity of the antiseptic is correct. The chosen surfactant is a non-ionic surfactant with a hydrophilic/lipophilic balance (HLB) greater than 10, preferably greater than 14, i.e. one predominantly of distinctly hydrophilic character. This surfactant must preferably be present in an amount of 1 to 6% by weight in the formulation. Among the commercially available products suitable for carrying out the invention, preference is given e.g. to polyethoxylated sorbitol esters, especially the polysorbate 80 available under the reference Montanox 80 from SEPPIC, which has a hydrophilic/lipophilic balance (HLB) of about 15 to 16.

Conventionally the formulation also comprises additives for ensuring the stability of the product, examples being antioxidants or photoprotective agents.

The elastomeric mass constituting the contact layer of the compress is produced by a hot-melt process in which the various constituents are mixed hot, the hydrocolloid and the active substance being added after a homogeneous mixture of the elastomers and the oily plasticizer has been obtained. The resulting mixture is then coated onto a flexible substrate which is easily shaped, for example a film or a non-woven or woven fabric, to give a dressing applicable directly to the skin.

In one of the preferred embodiments of the invention, the molten mixture can also be coated onto a wide-mesh woven fabric so that the threads constituting the fabric are totally coated and the mesh apertures are left unobstructed. The woven fabric used to produce this novel compress is preferably composed of synthetic threads with long fibers. This gives a discontinuous layer reinforced by the net, which is very easily shaped and which combines properties favorable to healing with the antiseptic property.

This antiseptic compress, which is used analogously to a tulle gras, can be brought into direct contact with a wound or burn, covered with an absorbent pad and held with tape or adhesive.

By way of example, a compress (E1) was produced from an elastomeric mass prepared by the hot-melt process from 1.52 kg of paraffin oil (obtained from SHELL under the reference ONDINA 15), 100 g of high molecular SEBS elastomer (Kraton G 1651 marketed by SHELL), 100 g of officinal petrolatum, 2.5 g of phenolic antioxidant, 300 g of finely powdered sodium carboxymethyl cellulose (ref. 7H4XF marketed by AQUALON), 100 g of polysorbate 80 (marketed under the reference MONTANOX 80 by SEPPIC) and 60 g of finely powdered silver sulfadiazine (of USP grade). The molten mass was coated onto an open-mesh woven fabric of the marquisette type made of 33 dtex polyester threads and having square meshes with an aperture of about 1 mm$^2$. The fabric is coated by passage through a bath of the molten elastomeric mass at 135–145° C. after which the excess gel is removed by rolling between two cylinders. The strip of coated fabric is quickly cooled in a stream of cold air. The amount of gel deposited on the threads is about 145 g/m$^2$, which corresponds to about 4 g/m$^2$ of silver sulfadiazine. The strip obtained is subsequently laminated with a protective film of opaque polyester on each side, then cut into fragments of appropriate size for use as a compress, and finally packaged in a leaktight sachet.

The antiseptic character of the compress (E1) according to the invention, produced above, was tested in vitro by contact with a culture medium. The following were used for comparison in this study:

a) a control compress (A) whose formulation is analogous to that of the compress (E1) above except that it contains neither active principle nor surfactant;

b) a compress (B) whose formulation is analogous to that of the compress (E1) and contains the active principle (i.e. 2.75% of silver sulfadiazine) but no surfactant; and c) a compress (C) of a type analogous to that described as the control (A). i.e. without active principle or surfactant, on which a 3 mm layer of Flammazine gel has been deposited, this method being common practice in hospitals. Flammazine is an emulsified cream containing 1% of silver sulfadiazine.

The tests were performed on two bacterial strains: *Staphylococcus aureus* and *Pseudomonas aeruginosa*, which are frequently responsible for nosocomial infections and/or superinfections in major burns. Disks 10 mm in diameter are cut out of each of the compresses to be tested and are deposited on geloses which have been inoculated in the bulk or on the surface with a bacterial suspension of known titer. After incubation for 24 hours at 37° C., the diameters of the zones of bacterial growth inhibition are measured and compared.

This experiment used trypcase-soya gelose (G1) or Mueller-Hinton 2 gelose (G2) (both supplied by BIOMERIEUX), which were inoculated in the bulk with 1 ml of a bacterial suspension with a titer of about $10^9$ or $10^6$ CFU/ml per 15 to 18 ml of gelose, or on the surface with 1 ml of a bacterial suspension with a titer of about $10^8$ CFU/ml (CFU=Colony Forming Unit). The results obtained, represented by the diameter of the inhibition zones expressed in mm, are shown in Tables 1 to 3.

TABLE 1

*Pseudomonas aeruginosa* $10^9$ CFU/ml

| Compress | G1 bulk | G1 surface | G2 bulk | G2 surface |
|---|---|---|---|---|
| A | 10 | 10 | 10 | 10 |
| B | 10 | 10 | 10.5 | 10.5 |
| C | 13 | 12 | 12 | 11 |
| E1 | 15 | 13 | 15 | 14 |

TABLE 2

*Staphylococcus aureus* $1.2.10^9$ CFU/ml

| Compress | G1 bulk | G1 surface | G2 bulk | G2 surface |
|---|---|---|---|---|
| A | 10 | 10 | 10 | 10 |
| B | 10 | 11 | 10 | 10 |
| C | 12 | 12 | 11 | 10 |
| E1 | 11 | 14 | 12 | 10.5 |

TABLE 3

Mueller Hinton 2 gelose inoculated in the bulk

| | *Pseudomonas aeruginosa* $2.9 \times 10^6$ CFU/ml | *Staphylococcus aureus* $2.1 \times 10^8$ CFU/ml |
|---|---|---|
| A | 10 | 10 |
| B | 10.5 | 11.5 |
| C | 17 | 16.5 |
| E1 | 17 | 16 |

In the above Tables, a result of 10 denotes that no zone around the compress disk of diameter 10 mm is devoid of bacterial growth.

Results above 10 denote that a peripheral zone around the compress is devoid of bacterial growth.

Table 1 relates to inhibition of the growth of *Pseudomonas aeruginosa* on the two types of gelose inoculated in the bulk or on the surface at a concentration of the order of $10^9$ CFU/ml. Table 2 relates to the same type of experiment performed with *Staphylococcus aureus*. Table 3 relates to inhibition of the growth of both bacterial strains at concentrations of the order of $10^6$ CFU/ml.

As expected, the results obtained show a total inactivity of the compress devoid of active substance (A), a very weak antiseptic activity of the compress containing the active substance but no surfactant, and a good inhibition of bacterial growth in the presence of the compress according to the invention (E1), the inhibition obtained generally be at least equivalent to that obtained in the presence of the compress associated with a thick layer of Flammazine. The results also confirm the need for the presence of a surfactant of hydrophilic type in order to make the antiseptic bioavailable at the surface to be rendered aseptic.

The absorption capacity of a contact layer produced with the elastomeric mass according to the above Example was measured and compared with an adhesive hydrocolloid mass such as that described in document FR 2775903. A continuous layer of the mixture formulated according to Example E1 of the present invention, weighing about 600 $g/m^2$, was produced for this test. The Comparative Example corresponds to the absorbent adhesive mass according to Example 1 of document FR 2775903, weighing 350 $g/m^2$. To measure the absorption capacity, a 25 $cm^2$ sample of each of the products was immersed for one hour in isotonic solution kept at 37° C. When the immersion time had elapsed the samples were drained and weighed. The weight increases calculated from these results show an absorption capacity of 144 $g/m^2$ for the Example according to the present invention and 1575 $g/m^2$ for the Comparative Example. Expressed as percentages by weight, the weight increases are respectively 144/600=24% for the Example according to the invention and 1575/350=450% for the Comparative Example.

The dressings obtained using a compress according to the invention thus have numerous advantages for the treatment of wounds or burns accompanied by a risk of infection: their composition makes it possible simultaneously to obtain a non-adhesive greasy contact through the presence of an oil or petrolatum, a moist environment through the presence of a hydrocolloid, and an aseptic medium created by a sufficient diffusion of an antiseptic. Furthermore, the structure of the elastomeric layer, which forms the contact layer together with the other ingredients, enables the dressing to be handled easily and removed gently and painlessly without leaving material originating from the contact layer on the newly regenerated tissues.

What is claimed is:

1. A compress for the treatment of wounds or burns, said compress having a surface in contact with the wound or burn consisting of an elastomeric matrix plasticized with a non-polar oil, said elastomeric matrix containing in dispersion a hydrocolloid, at least one antiseptic and at least one surfactant with a hydrophilic/lipophilic balance (HLB) greater than 10, said non-polar oil representing 55 to 90% of the weight of the compress.

2. A compress according to claim 1, wherein the above-mentioned elastomeric matrix consists of a synthetic elastomer of the tri-block type.

3. A compress according to claim 1, wherein the non-polar oil is selected from the group consisting of paraffin oils, officinal petrolatum and mixtures of these compounds.

4. A compress according to claim 1, wherein the hydrocolloid is sodium carboxymethyl cellulose.

5. A compress according to claim 1, wherein the surfactant is of the non-ionic type and is selected from the group consisting of polyethoxylated derivatives of sorbitol fatty acid esters.

6. A compress according to claim 1, wherein the antiseptic is a silver salt.

7. A compress according to claim 1, wherein the contact surface with the wound is that of a discontinuous layer which has been coated onto a wide-mesh woven substrate in such a way as to coat the threads of the fabric totally and leave the mesh apertures essentially unobstructed.

8. A dressing comprising a compress according to claim 1 said compress being placed on a substrate consisting of a film or a flexible nonwoven capable of being rendered adhesive.

9. A compress according to claim 1, wherein the above-mentioned elastomeric matrix consist of a synthetic elastomer of the tri-block type having a central block, said elastomer being selected from the group consisting of high molecular copolymers of polystyrene blocks and polyethylene-butylene blocks (SEBS) and high molecular copolymers of polystyrene blocks and polyethylene-propylene blocks (SEPS).

* * * * *